(12) United States Patent
Yu et al.

(10) Patent No.: US 12,279,887 B2
(45) Date of Patent: Apr. 22, 2025

(54) FLEXIBLE SWEAT-ACTIVATED GRAPHENE-COATED Ni FOAM-BASED Mg—$O_2$ BATTERY FOR STRETCHABLE MICROELECTRONICS FOR CONTINUOUS BIOMARKER MONITORING

(71) Applicant: City University of Hong Kong, Hong Kong (CN)

(72) Inventors: Xinge Yu, Hong Kong (CN); Xingcan Huang, Hong Kong (CN); Yiming Liu, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 842 days.

(21) Appl. No.: 17/453,192

(22) Filed: Nov. 2, 2021

(65) Prior Publication Data
US 2023/0135555 A1    May 4, 2023

(51) Int. Cl.
| | |
|---|---|
| A61B 5/00 | (2006.01) |
| A61B 5/145 | (2006.01) |
| B32B 5/02 | (2006.01) |
| B32B 5/24 | (2006.01) |
| B32B 15/14 | (2006.01) |
| D06M 11/13 | (2006.01) |
| H01M 4/38 | (2006.01) |
| H01M 4/96 | (2006.01) |
| H01M 8/0232 | (2016.01) |
| H01M 12/04 | (2006.01) |
| D06M 101/06 | (2006.01) |

(52) U.S. Cl.
CPC ........ *A61B 5/6833* (2013.01); *A61B 5/14517* (2013.01); *B32B 5/02* (2013.01); *B32B 5/245* (2013.01); *B32B 15/14* (2013.01); *D06M 11/13* (2013.01); *H01M 4/381* (2013.01); *H01M 4/96* (2013.01); *H01M 8/0232* (2013.01); *H01M 12/04* (2013.01); *A61B 2560/0214* (2013.01); *A61B 2562/164* (2013.01); *B32B 2266/06* (2013.01); *D06M 2101/06* (2013.01); *H01M 2300/0002* (2013.01)

(58) Field of Classification Search
None
See application file for complete search history.

(56) References Cited

PUBLICATIONS

She, D., Tsang, M., & Allen, M. (2019). Biodegradable batteries with immobilized electrolyte for transient MEMS. Biomedical Microdevices, 21(1). https://doi.org/10.1007/s10544-019-0377-x (Year: 2019).*

Bandodkar et al (2020). Sweat-activated biocompatible batteries for epidermal electronic and microfluidic systems. Nature Electronics, 3(9), 554-562. (Year: 2020).*

(Continued)

*Primary Examiner* — John R Downey
*Assistant Examiner* — Anant A Gupta
(74) *Attorney, Agent, or Firm* — S&F/WEHRW

(57) ABSTRACT

The present disclosure provides a stretchable and flexible sweat-activated graphene-coated Ni foam-based Mg—$O_2$ battery capable of powering an intelligent and flexible electronics for health monitoring purposes with different biosensors.

18 Claims, 11 Drawing Sheets

(56) References Cited

PUBLICATIONS

Bandodkar et al., "Sweat-activated biocompatible batteries for epidermal electronic and microfluidic systems," Nature Electronics, vol. 3, No. 9, pp. 554-562, Sep. 1, 2020 2020, doi: 10.1038/s41928-020-0443-7.

Garay et al., "Biofluid Activated Microbattery for Disposable Microsystems," Journal of Microelectromechanical Systems, vol. 24, No. 1, pp. 70-79, 2015, doi: 10.1109/JMEMS.2014.2317177.

Koo et al., "High performance magnesium anode in paper-based microfluidic battery, powering on-chip fluorescence assay," Biomicrofluidics, vol. 8, No. 5, p. 054104, 2014, doi: 10.1063/1.4894784.

Li et al., "Flexible cellulose based polypyrrole-multiwalled carbon nanotube films for bio-compatible zinc batteries activated by simulated body fluids," Journal of Materials Chemistry A, vol. 1, No. 45, pp. 14300-14305, 2013, doi: 10.1039/C3TA13137H.

Ortega et al., "Self-powered smart patch for sweat conductivity monitoring," Microsystems & Nanoengineering, vol. 5, No. 1, p. 3, Jan. 28, 2019 2019, doi: 10.1038/s41378-018-0043-0.

She et al., "Biodegradable batteries with immobilized electrolyte for transient MEMS," Biomedical Microdevices, vol. 21, No. 1, p. 17, Feb. 12, 2019 2019, doi: 10.1007/s10544-019-0377-x.

Xin et al., "Porous Mg thin films for Mg—air batteries," Dalton Transactions, 10.1039/C3DT52482E vol. 42, No. 48, pp. 16693-16696, 2013, doi: 10.1039/C3DT52482E.

Jia et al., "Toward Biodegradable Mg—Air Bioelectric Batteries Composed of Silk Fibroin—Polypyrrole Film," Advanced Functional Materials, vol. 26, No. 9, pp. 1454-1462, Mar. 1, 2016 2016, doi: https://doi.org/10.1002/adfm.201503498.

Li et al., "Metallic Magnesium Nano/Mesoscale Structures: Their Shape-Controlled Preparation and Mg/Air Battery Applications," Angewandte Chemie International Edition, vol. 45, No. 36, pp. 6009-6012, Sep. 11, 2006 2006, doi: https://doi.org/10.1002/anie.200600099.

\* cited by examiner

FLEXIBLE SWEAT-ACTIVATED GRAPHENE-COATED Ni FOAM-BASED Mg—O$_2$ BATTERY FOR STRETCHABLE MICROELECTRONICS FOR CONTINUOUS BIOMARKER MONITORING

TECHNICAL FIELD

The present invention is related to a flexible sweat-activated battery capable of powering an intelligent and flexible electronics for health monitoring purposes.

BACKGROUND

According to a statistics report, the wearable segment has projected revenue of US$17,834m in 2021, with an expected annual growth rate of 0.04%. The wearable segment includes devices equipped with sensors to track activity and health, which are explicitly intended for fitness.

There are many commercially available wearable devices, but most of them need a coin-cell or thin-film battery to power their system. These traditional batteries are classified as hazardous material, and there are certainly safety concerns for using them in contact with human skin. Additionally, they are not stretchable or flexible.

Certain academic publications introduce a biofluid-activated source of energy. While the choice of substrate varied, the reported batteries were flexible and biocompatible. The biofluids used for activation included sweat, blood, urine, saliva, and simulated body fluids, depending on whether the battery would be used to power external wearable electronics or implantable bioelectronics.

Among the reported batteries, the choice of anode, cathode, and electrolyte differed, leading to varying electrical performances. One of the batteries was sweat-activated with Mg anode, Ag/AgCl cathode, and an operating voltage of ~1.6V. Another biofluid-activated micro battery reported 1.75V maximum output voltage, 7.17 µAh capacity, 46% maximum efficiency. An open circuit potential of 2.2V and 3.0 mW/cm$^2$ power density was reported in a paper-based galvanic cell with Mg foil anode and Ag foil cathode in cellulose chip.

Aside from biofluid-activated energy sources, other Mg-air batteries with various fabrication techniques and morphologies have also been reported. One Mg-air battery was made from a porous Mg thin film with an open-circuit voltage of 1.41V and a discharge capacity of 821 mA·h·g$^{-1}$. Another bioelectric thin-film battery with a silk fibroin-polypyrrole film cathode and Mg alloy anode in PBS electrolyte was reported to have a specific energy density of ~4.70 mW·h·cm$^{-2}$. An Mg-air battery synthesized from Mg sea-urchin-like nanostructures had an energy density of 565 W·h·kg$^{-1}$ at discharge current density 5 mA/cm$^2$ and an open-circuit voltage of 1.4V. However, the reported batteries still have many difficulties to apply to many wearable devices in the market in view of their energy sources, structures, materials used and/or limited output power.

A need therefore exists for an improved battery for wearable devices that eliminates or at least diminishes the disadvantages and problems described above.

SUMMARY

The present disclosure proposes a stretchable and flexible sweat-activated graphene-coated Ni foam-based Mg—O$_2$ battery capable of powering an intelligent and flexible electronics for health monitoring purposes with different biosensors.

The proposed battery in certain embodiments is based on the oxidation-reduction reaction (redox) between magnesium and oxygen. A thin layer of Mg and a nickel foam coated with graphene are working as the electrodes. Cotton with high absorption capabilities is placed between the Mg sheet and the skin, helping to absorb the sweat. Another cotton doped with KCl is placed between two electrodes. It works as the salt bridge and allows ion flow once it absorbs the sweat. A porous adhesive tape is a substrate for the battery parts while allowing the oxygen to pass through it easily.

Provided herein is a first fabric layer arranged to cover a skin of a user and used for absorbing sweat from the skin; a magnesium (Mg) sheet; a salt-doped fabric layer comprising a second fabric layer doped with particles of a potassium salt or a sodium salt, the Mg sheet being located between the first fabric layer and the salt-doped fabric layer, the first fabric layer and the salt-doped fabric layer being arranged to be partially overlapped for allowing the salt-doped fabric layer to absorb sweat from the first fabric layer; a graphene-coated Ni foam comprising a Ni foam and a graphene layer covering the Ni foam, the graphene layer being located between the Ni foam and the salt-doped fabric layer; and a porous tape covering the Ni foam and comprising pores for allowing oxygen from environment to flow into the Ni foam.

In certain embodiments, the first fabric layer comprises cotton, spandex, nylon or linen.

In certain embodiments, the second fabric layer comprises cotton, spandex, nylon or linen.

In certain embodiments, the potassium salt is potassium chloride (KCl).

In certain embodiments, the sodium salt is sodium chloride (NaCl).

In certain embodiments, the Mg sheet is connected to a first conductive wire; and the Ni foam is connected to a second conductive wire.

In certain embodiments, the porous tape further comprises a central portion and a peripheral portion, the central portion covering the Ni foam, the peripheral portion being arranged to be attached to the skin.

In certain embodiments, the porous tape further comprises an adhesive surface for attaching the porous tape to the Ni foam and the skin.

Provided herein is a wearable device for measuring one or more biomarkers comprising: one or more sensors for measuring the one or more biomarkers respectively; a microcontroller for collecting data of the one or more sensors; and one or more flexible sweat-activated batteries described above for powering the microcontroller.

In certain embodiments, the one or more biomarkers include body temperature, pulse rate (PR), exercise intensity, peripheral capillary oxygen saturation (SpO$_2$), or a combination thereof.

In certain embodiments, the one or more sensors include a temperature sensor, a PR sensor, an accelerometer, a SpO$_2$ sensor, or a combination thereof.

In certain embodiments, the wearable device further comprises: a voltage regulator connected to the one or more flexible sweat-activated batteries for providing a stable voltage to the microcontroller; a Bluetooth module for allowing the microcontroller to send the collected data to a user interface; and a flexible printed circuit board, on which the microcontroller, the voltage regulator, the Bluetooth module are mounted.

In certain embodiments, the one or more flexible sweat-activated batteries are configured to provide a voltage of 2.5V to 5.2V; and the voltage regulator is configured to provide the stable voltage with 3.3V.

In certain embodiments, the one or more flexible sweat-activated batteries include four flexible sweat-activated batteries.

In certain embodiments, the wearable device further comprises: a first flexible layer arranged to cover a skin of the user; and a second flexible layer, the flexible printed circuit board being located between the first flexible layer and the second flexible layer.

In certain embodiments, the first flexible layer comprises a hole accommodating the one or more sensors.

In certain embodiments, the wearable device further comprises: two conductive wires for connecting the one or more flexible sweat-activated batteries to the flexible printed circuit board; and a flexible substrate comprising one or more holes accommodating the one or more flexible sweat-activated batteries.

In certain embodiments, the user interface is a smartphone application contained in a smartphone.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects of the present invention are disclosed as illustrated by the embodiments hereinafter.

BRIEF DESCRIPTION OF DRAWINGS

The appended drawings, where like reference numerals refer to identical or functionally similar elements, contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which.

Figure 1A:
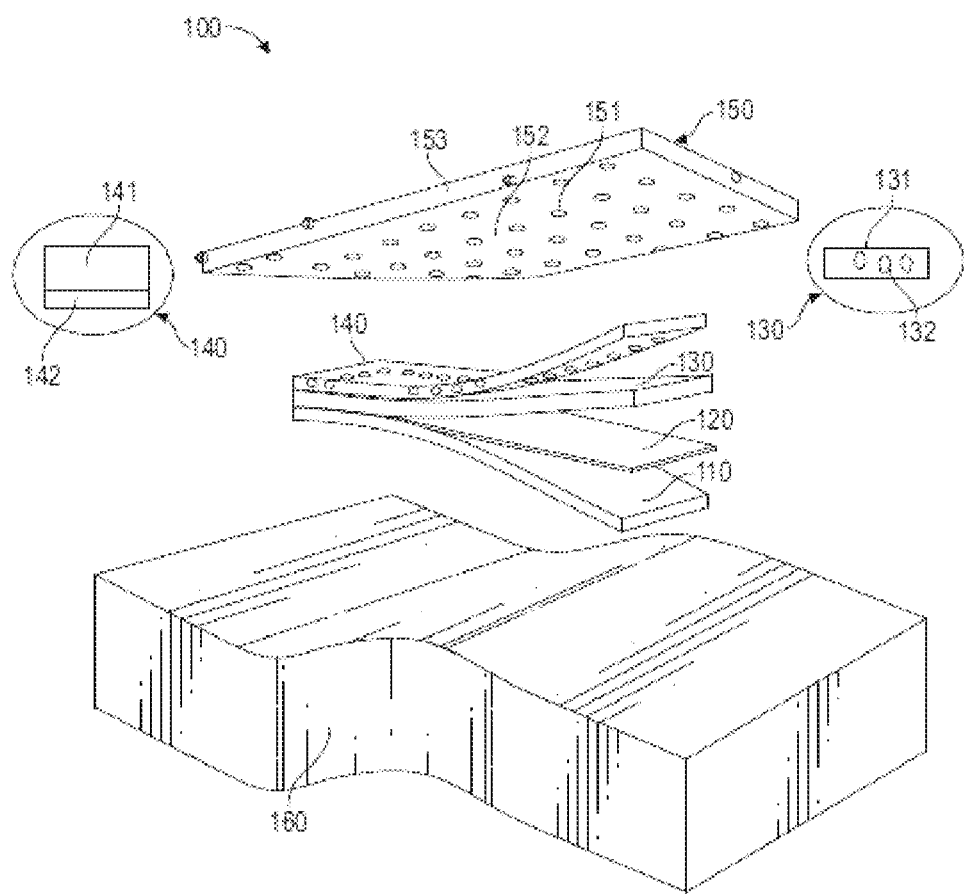
FIG. 1A shows an exploded view of the layer-by-layer structure of a flexible sweat-activated battery (FSAB) according to certain embodiments.

Skilled artisans will appreciate that elements in the figures are illustrated for simplicity and clarity and have not necessarily been depicted to scale.

DETAILED DESCRIPTION OF THE INVENTION

It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

The present disclosure proposes a flexible sweat-activated battery comprising highly biocompatible materials and flexible substrates. As a result, using this flexible sweat-activated battery does not have any safety concerns in contact with human skin.

The flexible sweat-activated battery is a graphene-paper based $Mg$—$O_2$ battery, which is sweat-activated and can power any skin-interfaced external wearables. The flexible sweat-activated battery uses an Mg sheet as the anode, oxygen as cathode, and graphene sheet as a catalyst. Two FSABs provide a voltage of 1.8-3V to power the stretchable microelectronic circuit. Problems like electrolyte leakage are mitigated due to the dry nature of the proposed FSAB. Also, they are flexible, stretchable, and biocompatible. Hence, they can conveniently power skin-interfaced wearable electronics.

Certain embodiments provide a first fabric layer arranged to cover a skin of a user and used for absorbing sweat from the skin; a Mg sheet; a salt-doped fabric layer comprising a second fabric layer doped with particles of a potassium salt or a sodium salt, the Mg sheet being located between the first fabric layer and the salt-doped fabric layer, the first fabric layer and the salt-doped fabric layer being arranged to be partially overlapped for allowing the salt-doped fabric layer to absorb sweat from the first fabric layer; a graphene-coated Ni foam comprising a Ni foam and a graphene layer covering the Ni foam, the graphene layer being located between the Ni foam and the salt-doped fabric layer; and a porous tape covering the Ni foam and comprising pores for allowing oxygen from environment to flow into the Ni foam.

In certain embodiments, the first fabric layer comprises cotton, spandex, nylon or linen, and the second fabric layer comprises cotton, spandex, nylon or linen.

In certain embodiments, the potassium salt is neutral and not irritating to the skin. Preferably, the potassium salt is potassium chloride.

In certain embodiments, the sodium salt is neutral and not irritating to the skin. Preferably, the sodium salt is sodium chloride.

Certain embodiments provide a flexible sweat-activated battery comprising: a first cotton layer arranged to cover on a skin of a user; a Mg sheet; a potassium chloride (KCl)-doped cotton layer comprising a second cotton layer doped with KCl particles, the Mg sheet being located between the first cotton layer and the KCl-doped cotton layer; a graphene-coated Ni foam comprising a Ni foam and a graphene layer covering the Ni foam, the graphene layer being located between the Ni foam and the KCl-doped cotton layer; and a porous tape covering the Ni foam and comprising pores for allowing oxygen from environment to flow into the Ni foam.

In certain embodiments, the Mg sheet is connected to a first conductive wire; and the Ni foam is connected to a second conductive wire.

In certain embodiments, the porous tape further comprises a central portion and a peripheral portion, the central portion covering the Ni foam, the peripheral portion being arranged to be attached to the skin.

In certain embodiments, the porous tape further comprises an adhesive surface for attaching the porous tape to the Ni foam and the skin.

The present disclosure further proposes a wearable device for measuring biomarkers comprising flexible sweat-activated batteries described above, biosensors and flexible electronics powered by the flexible sweat-activated batteries in order to monitor health. Through the biosensors, a lot of physiologically relevant information (e.g., sodium concentration of sweat, pH of sweat, skin impedance) can be gleaned through sweat analysis. An added advantage is that the collection is completely non-invasive and skin safe. Once the flexible sweat-activated batteries absorb sweat from the human body, they activate and power the flexible electronics in order to measure proper biomarkers.

Certain embodiments provide a wearable device for measuring one or more biomarkers comprising: one or more sensors for measuring the one or more biomarkers respectively; a microcontroller connected to the one or more sensors and used for collecting data of the one or more sensors; and one or more flexible sweat-activated batteries described above for powering the microcontroller.

In certain embodiments, the wearable device includes a stretchable microelectronic circuit fabricated on a soft substrate, containing different sensors to measure proper acceleration, peripheral capillary oxygen saturation, pulse rate, and body temperature, and sweat-activated batteries to provide power to the circuit.

In certain embodiments, the wearable device includes flexible smart electronics, four FSABs, an accelerometer, a $SpO_2$ sensor, a PR sensor and a temperature sensor. The wearable device monitors the subject's health using these sensors. It also contains a Bluetooth module, allowing the wearable device to communicate with a smartphone to display the collected data.

In certain embodiments, all parts of the wearable device, including FSABs, flexible electronic circuits, and sealing layers, are integrated into one patch, such that the user can conveniently use the wearable device during exercise or other physical activities.

As shown in FIG. 1A, a FSAB 100 according to certain embodiments is fabricated layer by layer. The FSAB 100 comprises a cotton layer 110, a Mg sheet 120, a KCl-doped cotton layer 130, a graphene-coated nickel (Ni/G) foam 140 and a porous tape 150, which are stacked together. The first layer that sits on a skin 160 is the cotton layer 110 (1 cm×3 cm) with high water absorption capability. The cotton layer 110 absorbs the secreted sweat on the skin 160. The next layer is the Mg sheet 120 (slight less than 1 cm×3 cm) working as an anode. The KCl-doped cotton layer 130 covering the Mg sheet 120 is a layer of cotton 131 doped with KCl particles 132 (shown in the right inset of FIG. 1A), which acts as the electrolyte layer and separator between anode and cathode. The KCl particles 132 are neutral salt particles with neutral character and not irritating to the skin as well as can provide better electrical performance than other salts. The areas of the cotton layer 110 and the KCl-doped cotton layer 130 are larger than that of the Mg sheet 120 such that the cotton layer 110 and the KCl-doped cotton layer 130 are partially overlapped at their periphery for allowing the KCl-doped cotton layer 130 to absorb the sweat from the cotton layer 110. Once the absorbed sweat reaches the KCl-doped cotton layer 130, the absorbed sweat allows ions (e.g., hydroxide ions) to flow between the Mg anode and oxygen cathode, functioning as an electrolyte. The next layer is the graphene-coated nickel foam 140 comprising a Ni foam 141 and a graphene layer 142 covering the Ni foam 141 (shown in the left inset of FIG. 1A). The Ni foam 141 is open-celled and acts a current collector and a gas diffusion layer. The graphene layer 142 is located between the Ni foam 141 and the KCl-doped cotton layer 130. The oxygen from the environment reduces in the graphene layer 142, the graphene of which acts as a catalyzing agent. The porous structure of the Ni foam 141 results in a significantly increased contact area between graphene and oxygen. As a result, the FSAB 100 yields remarkably better performance. Finally, a porous tape 150 with pores 151 and an adhesive surface on its bottom side is used as the substrate to hold the battery parts together. The porosity of the porous tape 150 allows the flow of oxygen atoms from the environment to the Ni foam 141. The porous tape 150 further comprises a central portion 152 and a peripheral portion 153, the central portion 152 covers the Ni foam 141, the peripheral portion 153 is attached to the skin 160.

The total redox reaction between magnesium and oxygen is as follows:

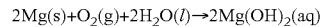

Magnesium oxidizes and loses two electrons, forming $Mg^{2+}$ ions. As a result, the oxidation half-reaction is as follows:

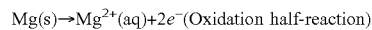

In Ni foam, oxygen atoms form hydroxide. As a result, oxygen reduces, and the reduction half-reaction is as follows:

$$O_2(g)+2H_2O(l)+4e^- \rightarrow 4OH^-(aq) \text{(Reduction half-reaction)}$$

Figure 1B:
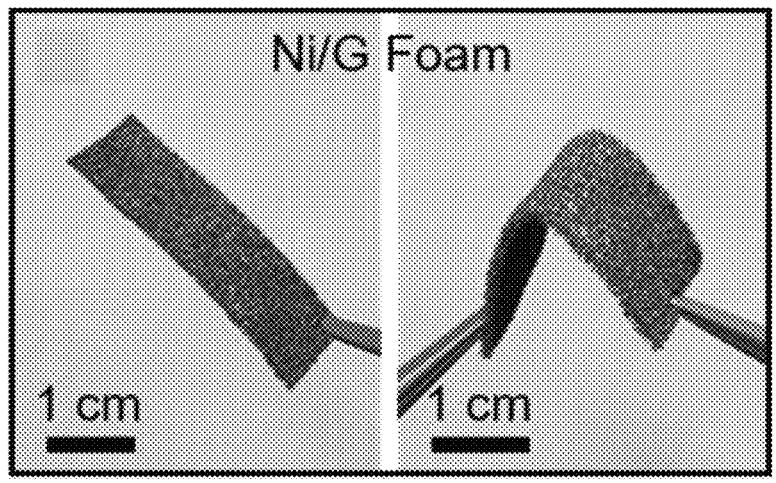
FIG. 1B shows a flexible Ni foam covered by a layer of graphene.
Figure 1C:
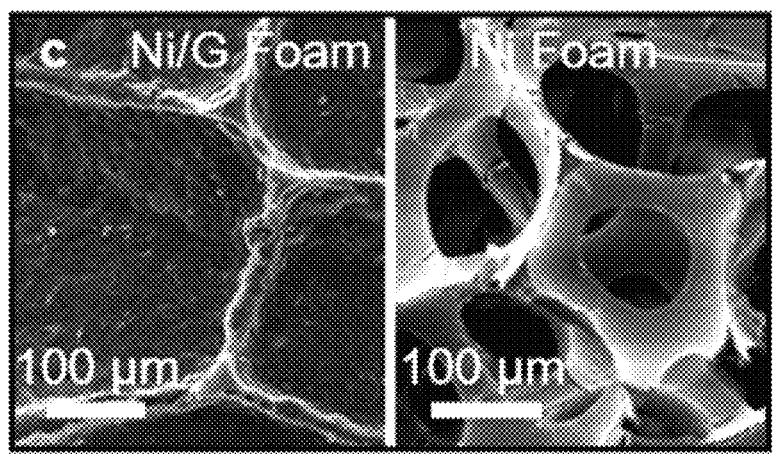
FIG. 1C shows scanning electron microscope (SEM) images of a graphene layer on a Ni foam (left) and a Ni foam without graphene (right)
Figure 1D:
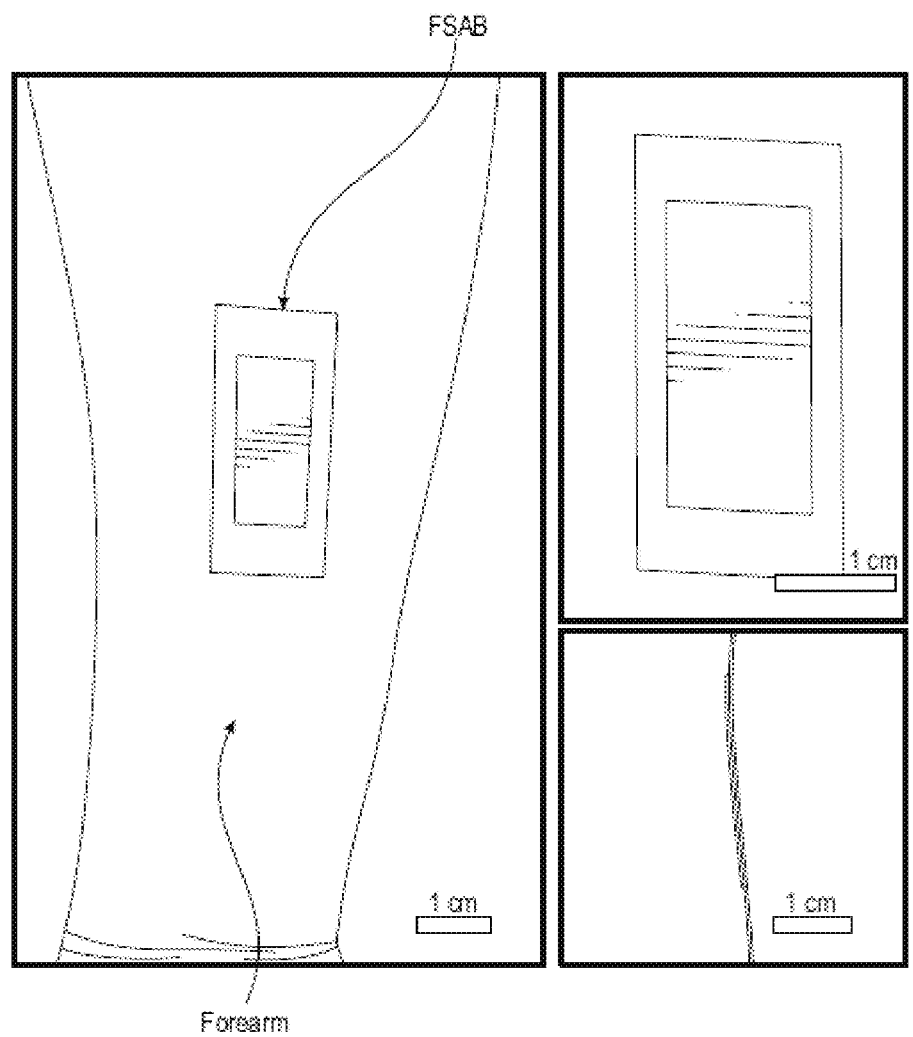
FIG. 1D shows the FSAB attached to the user's forearm.

A nickel foam covered by graphene and its flexibility is demonstrated in FIG. 1B. SEM images of the graphene layer and Ni foam are shown in FIG. 1C. Optical images of a flexible sweat-activated battery while being used on the user's forearm are demonstrated in FIG. 1D.

Figure 1E:
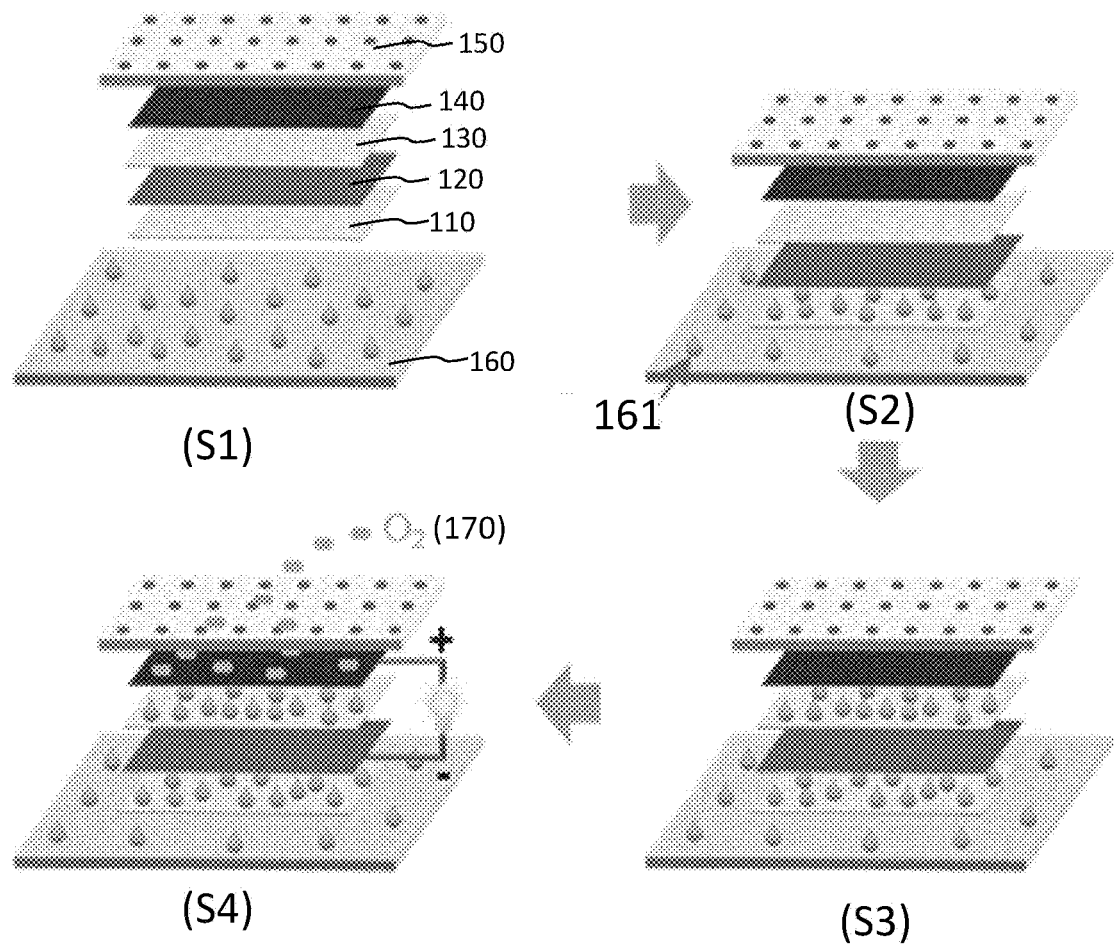
FIG. 1E shows the working principle of the FSAB.

The working principle of the flexible sweat-activated battery described above is shown in FIG. 1E. In step S1, the skin 160 secrete sweat 161. In step S2, when the cotton layer 110 is in contact with the skin 160, the cotton layer 110 absorbs the sweat 161. In step S3, the KCl-doped cotton layer 130 absorbs the sweat 161 from the cotton layer 110. In step S4, oxygen 170 from the environment flows into the Ni foam of the Ni/G foam 140 via the pores of the porous tape 150. Then, the Mg sheet 120 oxidizes and release electrons and $Mg^{2+}$ ions, and the oxygen 170 in the Ni foam reduces under the assistance of the graphene layer of the Ni/G foam 140 and reacts with $H_2O$ to form $OH^-$ ions such that a voltage is generated between the Mg sheet 120 and the oxygen 170 in the Ni foam.

Figure 2A:
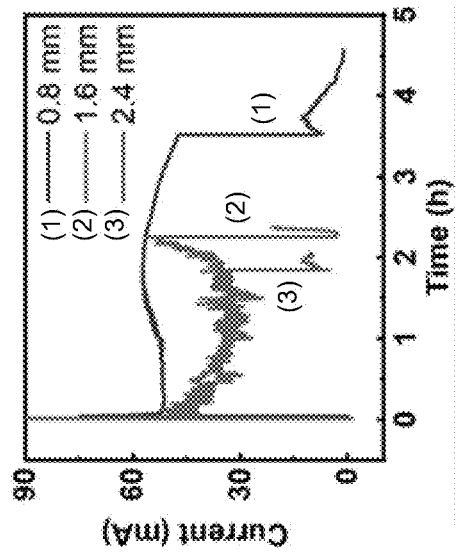
FIG. 2A shows the open-circuit output voltage of the FSABs with and without a graphene layer on a Ni foam.
Figure 2B:
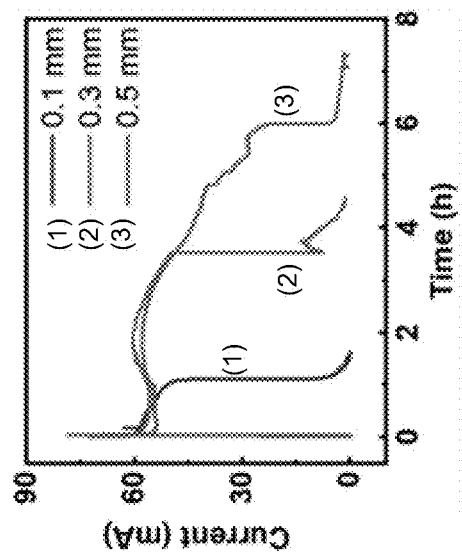
FIG. 2B shows the open-circuit output voltage of the FSABs for Mg sheets with different thicknesses.
Figure 2C:
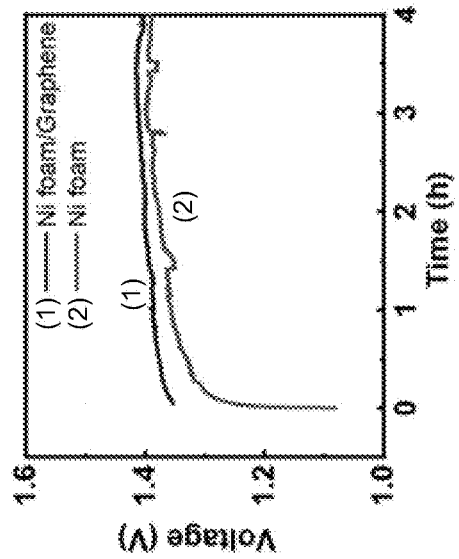
FIG. 2C shows the open-circuit output voltage of the FSABs for pieces of cotton with different thicknesses.
Figure 2D:
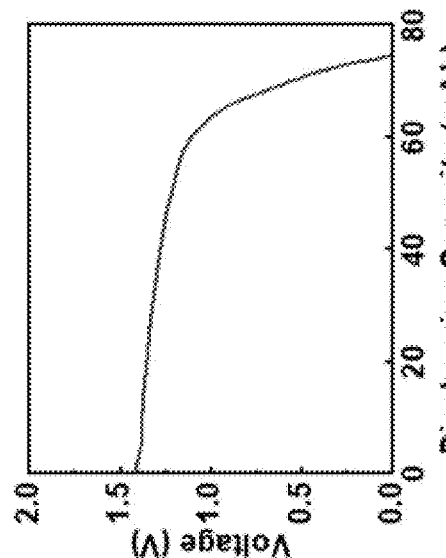
FIG. 2D shows the open-circuit output voltage of the FSAB as a proportion of its maximum output voltage by increasing the artificial sweat rate in a battery cell.
Figure 2E:
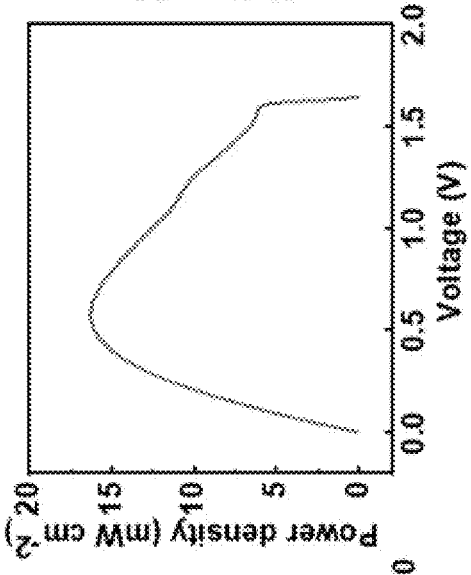
FIG. 2E shows the power density of the FSAB.
Figure 2F:
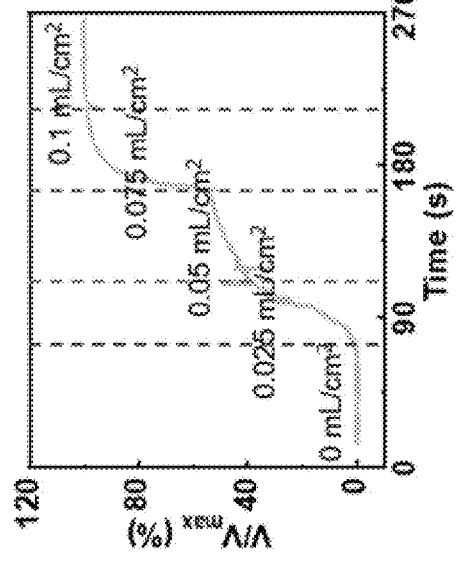
FIG. 2F shows the output voltage of the FSAB based on its discharging capacity.
Figures 2G, 2H, 2I:
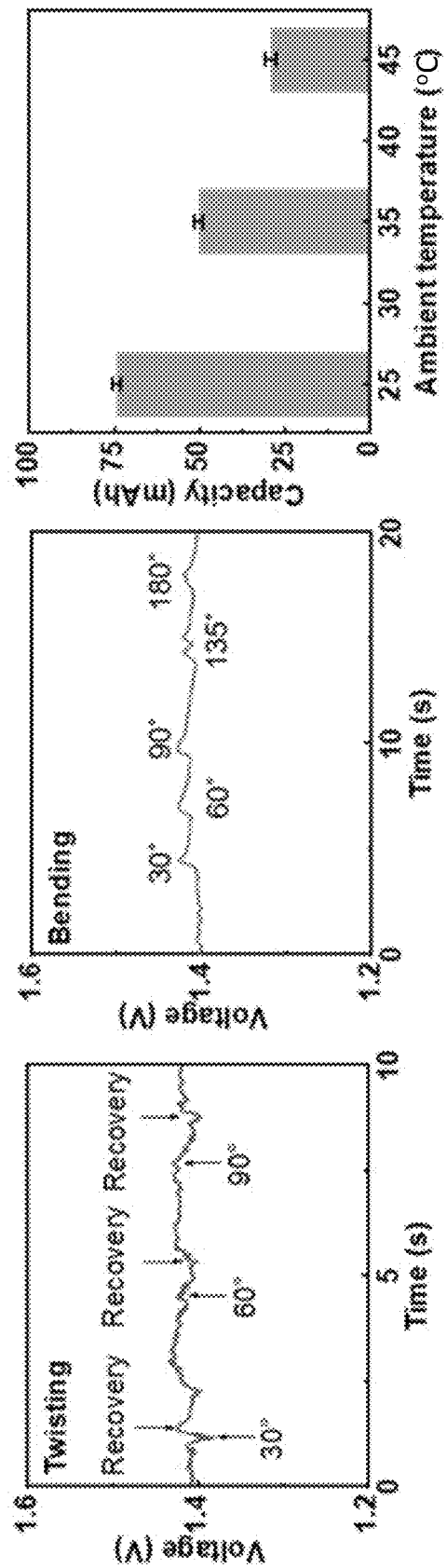
FIG. 2G shows the output voltage of the FSAB during twisting cycles with different angles.
FIG. 2H shows the output voltage of the FSAB during bending cycles with different angles.
FIG. 2I shows the FSAB's capacity in different ambient temperatures.

FIGS. 2A-2I show the electrical performance of the flexible sweat-activated battery. The open-circuit output voltage of the battery is compared when the graphene covers the Ni foam and the graphene is not used. FIG. 2A shows that the use of graphene results in a higher and more stable output voltage. The thickness of the Mg sheet directly influences the battery lifespan. The higher the Mg sheet thickness is, the longer battery can work as shown in FIG. 2B. The current measurements have been done while the battery is connected to a 2.5 resistance as the load. According to FIG. 2C, different layers of cotton with different thicknesses have been tested. With a thinner cotton layer, the battery works longer. As it is shown in FIG. 2D, once the sweat rate reaches 0.025 $mL/cm^2$, the battery activates. The output voltage reaches its maximum when the secreted sweat is 0.1 $mL/cm^2$ or more. The battery's power density and discharging capacity have been tested and presented in FIG. 2E and FIG. 2F, respectively. Accordingly, the maximum power density is 16.26 $mW·cm^{-2}$. The open-circuit output voltage of the battery has been measured through 45 consecutive twisting cycles. FIG. 2G shows the performance of the battery when it is twisted for 30°, 60°, and 90°. Twisting cycles and the recovery period are labeled in the graph, proving the reliable and stable performance of the battery under twisting. FIG. 2H similarly shows the battery performance in different bending cycles when it is bent by different angles between 30° and 180°. The battery capacity has also been measured in different temperatures. In room temperature, the battery shows the best performance as shown in FIG. 2I.

Figure 3A:
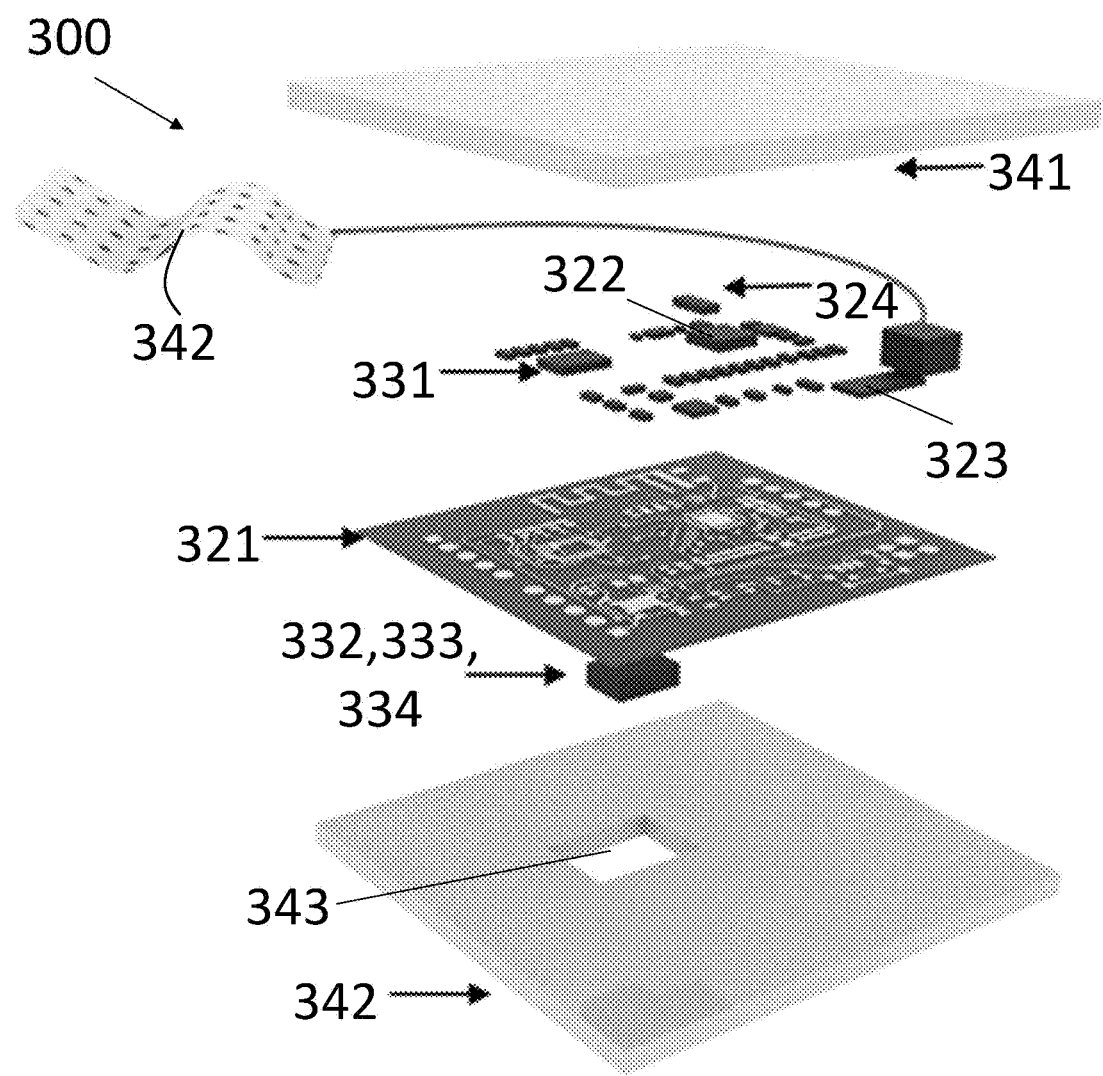
FIG. 3A shows an exploded view of a wearable device represented layer by layer according to certain embodiments.
Figure 3B:
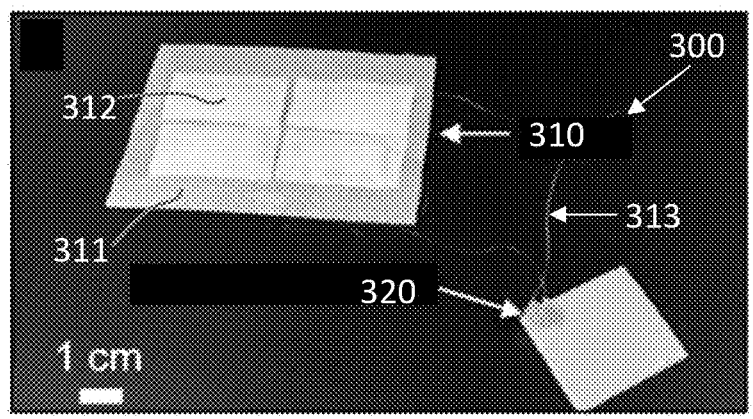
FIG. 3B shows four FSABs on a 8 cm×8 cm flexible substrate connected to a soft microelectronic patch with 3 cm×3 cm.
Figure 3C:
FIG. 3C shows the flexibility of the soft microelectronic patch under pressure.

FIGS. 3A and 3B show a wearable device 300 for measuring biomarkers comprising a battery patch 310 and a soft microelectronic patch 320 with layer-by-layer structure according to certain embodiments. The battery patch 310 comprises a soft PDMS substrate 311 and four FSABs 312 accommodated in the holes of the soft PDMS substrate 311, and the four FSABs 312 are connected to the soft microelectronic patch 320 through two thin wires 313 as shown in FIG. 3B. The battery patch 310 with four FSABs 312 is 8 cm×5 cm, and the soft microelectronic patch 320 occupies an area of 3 cm×3 cm. The soft microelectronic patch 320 comprises a flexible printed circuit board 321, a microcontroller 322, a voltage regulator 323, a Bluetooth module 324, an accelerometer 331, a $SpO_2$ sensor 332, a pulse rate sensor 333, a temperature sensor 334, a top PDMS layer 341 and a bottom PDMS layer 342. The microcontroller 322, the voltage regulator 323, the Bluetooth module 324 and the accelerometer 331 are mounted on the flexible printed circuit board 321, which is sandwiched by the top PDMS layer 341 and the bottom PDMS layer 342. The $SpO_2$ sensor 332, the pulse rate sensor 333, the temperature sensor 334 are accommodated in a hole 343 of bottom PDMS layer 342 for being in contact with a skin to measure the biomarkers. FIG. 3C shows the flexibility of the soft microelectronic patch.

Figure 3D:
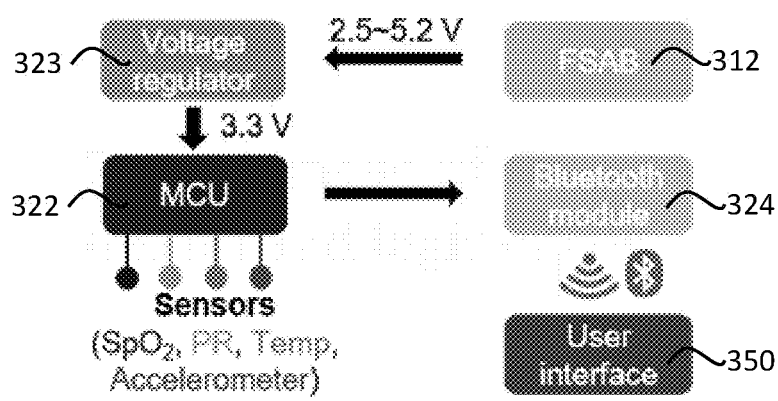
FIG. 3D shows the diagram of the wearable device's working principle.

The diagram in FIG. 3D explains the working principle of the wearable device 300. The FSABs 312 are connected to the voltage regulator 323 on the flexible printed circuit board 321 for providing a stable 3.3V voltage for the microcontroller 322. The microcontroller 322 is connected to the aforesaid biosensors and collects the data. The microcontroller 322 sends the collected data through the Bluetooth module 324 to a user interface 350, which is a smartphone app in this embodiment.

Figure 3E:
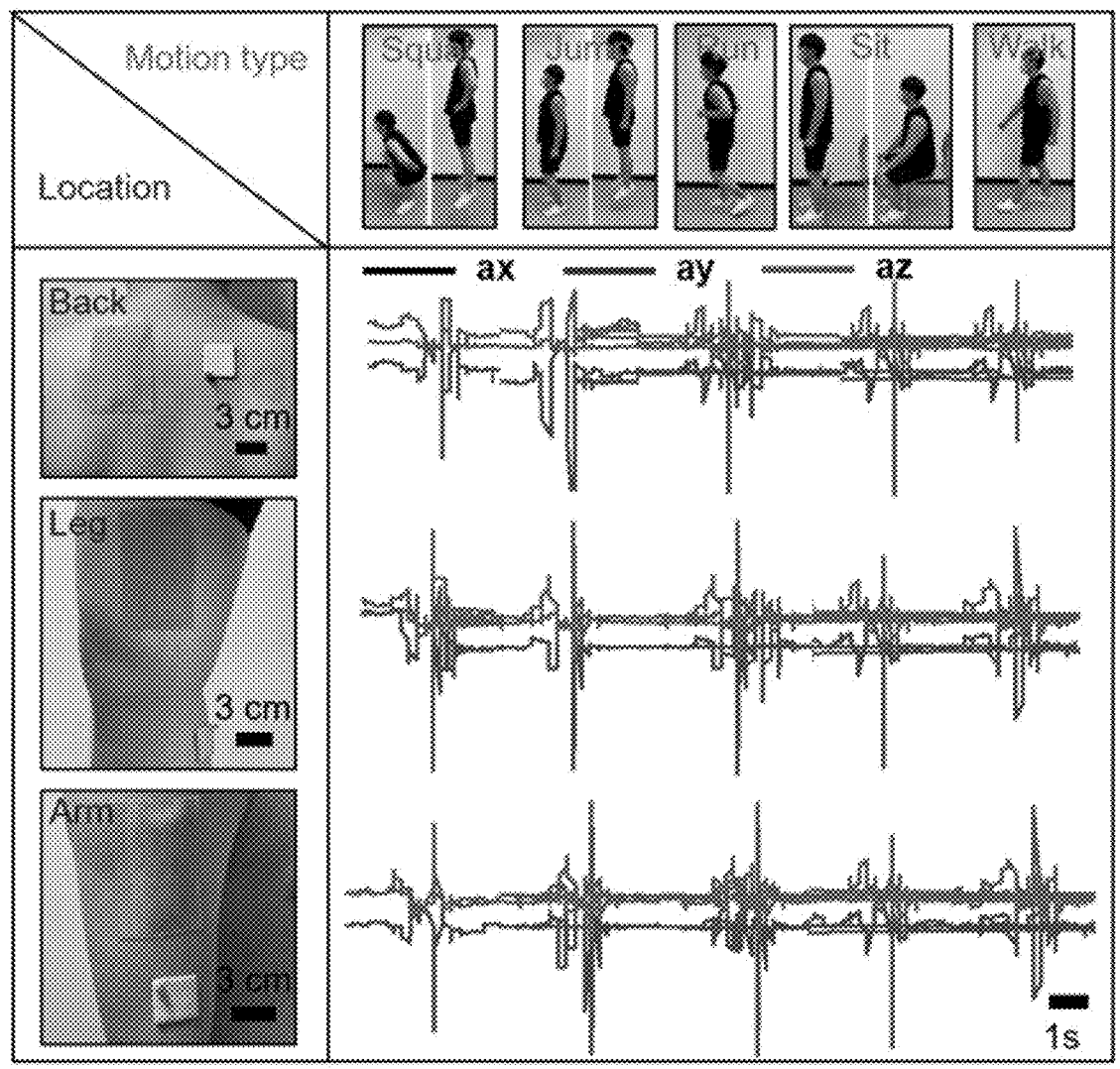
FIG. 3E shows output signals of the accelerometer sensor for different positions, including squatting, jumping, running, sitting, and walking, while the proposed wearable device is attached to three different places on the body.
Figure 3F:
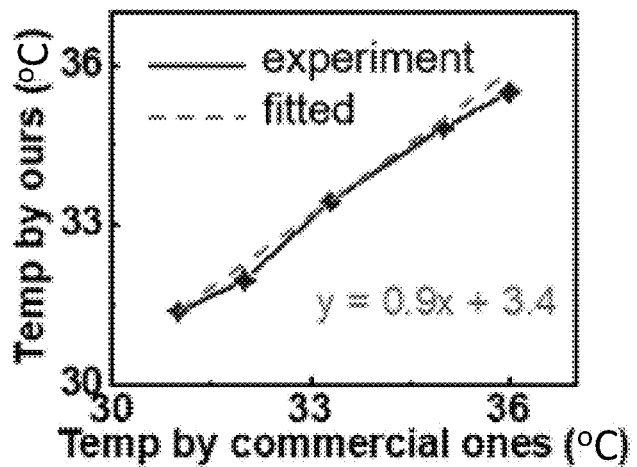
FIG. 3F shows a comparison between the body temperature measured by the proposed wearable device and a commercial device.
Figure 3G:
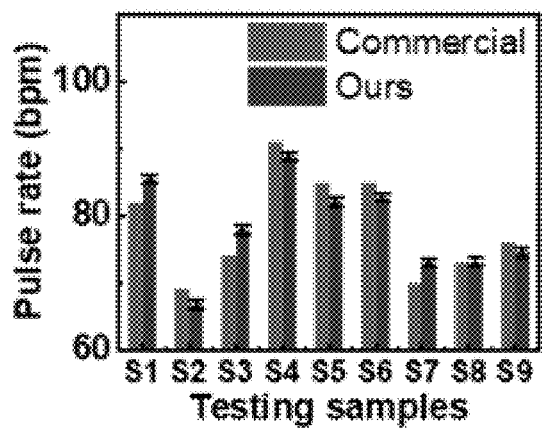
FIG. 3G shows a comparison between user's pulse rate measured by the proposed wearable device and a commercial device.
Figure 3H:
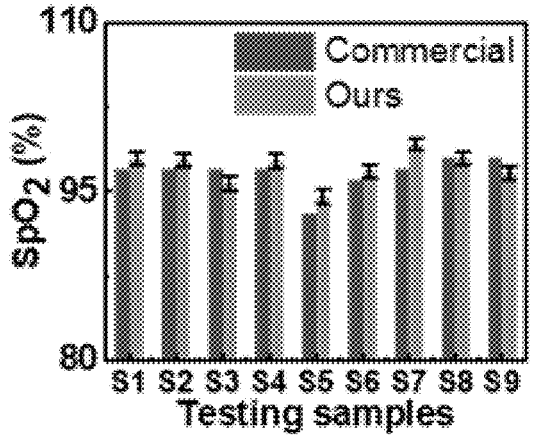
FIG. 3H shows a comparison between user's $SpO_2$ measured by the proposed wearable device and a commercial device.

FIG. 3E shows the accelerometer's output signals for different positions while the wearable device is attached to three different places, including the back, leg, and arm. The body temperature measured by the proposed wearable device is compared to results from a commercial sensor. FIG. 3F shows these temperature measurements, which evidence the excellent compatibility between the results. Pulse rate and $SpO_2$ have been measured simultaneously using the proposed wearable device and a commercial one. Results are reported in FIG. 3G and FIG. 3H, respectively, showing the excellent performance of the proposed wearable device.

Figure 4A:
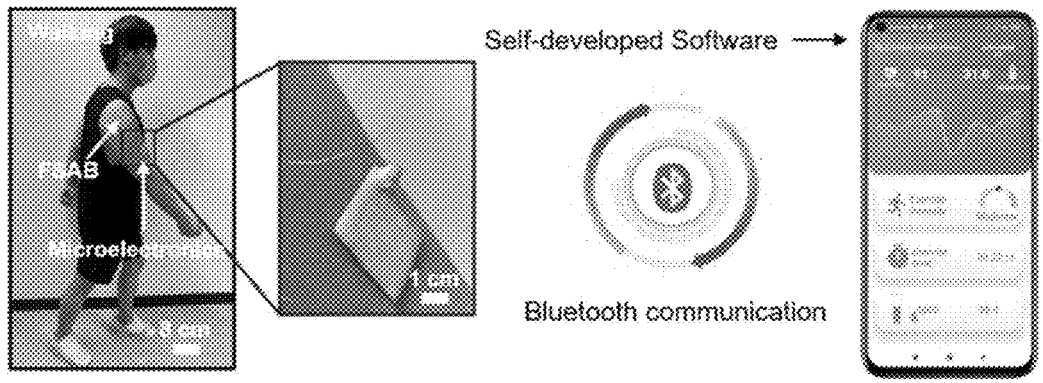
FIG. 4A shows a user wearing the proposed wearable device, connected to a smartphone through Bluetooth, while he is walking.
Figure 4B:
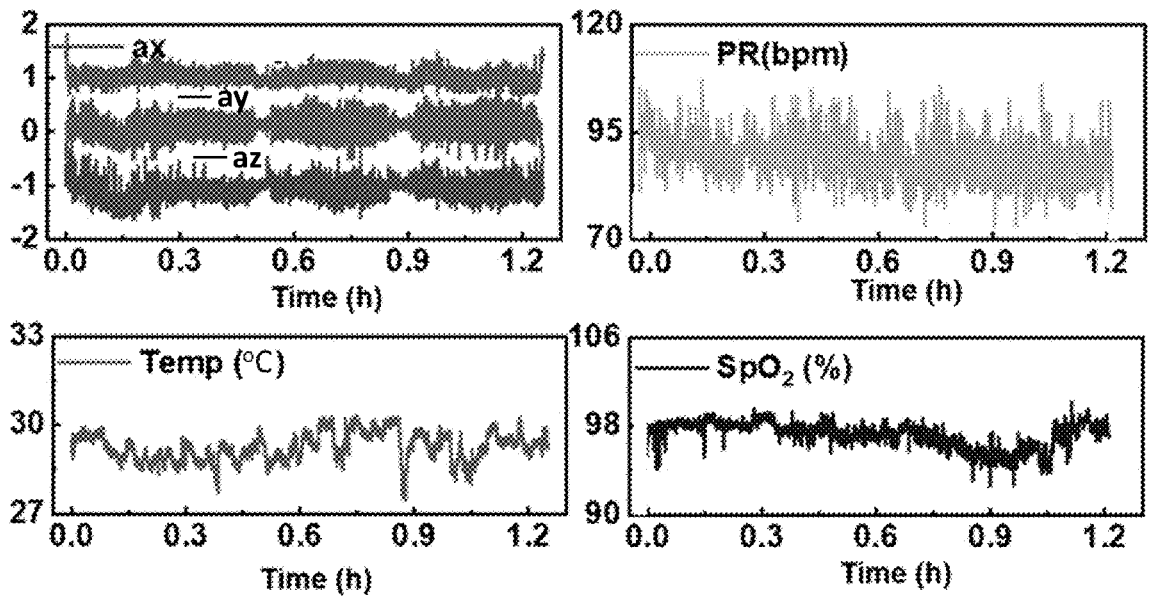
FIG. 4B shows output signals of the integrated sensors recorded by the proposed wearable device and transmitted to the smartphone during the user's exercise.
Figure 4C:
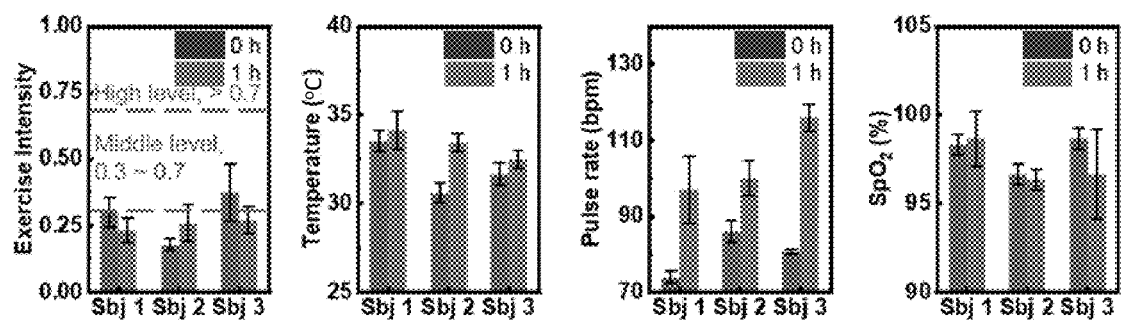
FIG. 4C shows a measurement of different biomarkers by the proposed wearable device, at the beginning of exercise and one hour after it, in three different subjects.

In order to show the performance of the proposed wearable device in a real-life situation, a user wear the proposed wearable device on his arm while walking as shown in FIG. 4A. A smartphone application is developed which is connected to the proposed wearable device and reads sensors' data. The output signals of all sensors, including accelerometer, pulse rate, body temperature, and $SpO_2$, are presented in FIG. 4B. Moreover, three different subjects used the proposed wearable device while exercising. They have self-reported their exercise intensity by a factor of 1. Sensors' data are collected at the beginning and one hour after exercising. As it has been shown in FIG. 4C, the temperature and pulse rate of all subjects have increased after one hour of exercise. The percentage of oxygen saturation has also been measured and reported.

Thus, it can be seen that an improved battery and wearable device have been disclosed which eliminates or at least diminishes the disadvantages and problems associated with prior art devices. The proposed battery is a biocompatible and flexible sweat-activated battery that can be activated by the secreted sweat from the human body during any physical activities. Accordingly, the proposed battery has a wide variety of applications in wearable electronics. The flexible sweat-activated battery can power wearable microelectronics in order to measure biomarkers. The proposed flexible microelectronics can be used for monitoring acceleration, $SpO_2$, PR and temperature for any individuals engaged in physical activities. Accordingly, the proposed wearable device can be used by any users working in healthcare facilities, sports centres, fitness rooms, and any other individual who has physical activities in their daily life.

Although the invention has been described in terms of certain embodiments, other embodiments apparent to those of ordinary skill in the art are also within the scope of this invention. Accordingly, the scope of the invention is intended to be defined only by the claims which follow.

What is claimed is:

1. A flexible sweat-activated battery comprising:
   a first fabric layer arranged to cover a skin of a user and used for absorbing sweat from the skin;
   a magnesium (Mg) sheet;
   a salt-doped fabric layer comprising a second fabric layer doped with particles of a potassium salt or a sodium salt, the Mg sheet being located between the first fabric layer and the salt-doped fabric layer, the first fabric layer and the salt-doped fabric layer being arranged to be partially overlapped for allowing the salt-doped fabric layer to absorb sweat from the first fabric layer;
   a graphene-coated Ni foam comprising a Ni foam and a graphene layer covering the Ni foam, the graphene layer being located between the Ni foam and the salt-doped fabric layer; and
   a porous tape covering the Ni foam and comprising pores for allowing oxygen from environment to flow into the Ni foam.

2. The flexible sweat-activated battery of claim 1, wherein the first fabric layer comprises cotton, spandex, nylon or linen.

3. The flexible sweat-activated battery of claim 1, wherein the second fabric layer comprises cotton, spandex, nylon or linen.

4. The flexible sweat-activated battery of claim 1, wherein the potassium salt is potassium chloride (KCl).

5. The flexible sweat-activated battery of claim 1, wherein the sodium salt is sodium chloride (NaCl).

6. The flexible sweat-activated battery of claim 1, wherein the Mg sheet is connected to a first conductive wire; and the Ni foam is connected to a second conductive wire.

7. The flexible sweat-activated battery of claim 1, wherein the porous tape further comprises a central portion and a peripheral portion, the central portion covering the Ni foam, the peripheral portion being arranged to be attached to the skin.

8. The flexible sweat-activated battery of claim 7, wherein the porous tape further comprises an adhesive surface for attaching the porous tape to the Ni foam and the skin.

9. A wearable device for measuring one or more biomarkers comprising:
   one or more sensors for measuring the one or more biomarkers respectively;
   a microcontroller for collecting data of the one or more sensors; and
   one or more batteries for powering the microcontroller, wherein an individual battery is realized by the flexible sweat-activated battery of claim 1.

10. The wearable device of claim 9, wherein the one or more biomarkers include body temperature, pulse rate (PR), exercise intensity, peripheral capillary oxygen saturation ($SpO_2$), or a combination thereof.

11. The wearable device of claim 9, wherein the one or more sensors include a temperature sensor, a PR sensor, an accelerometer, a $SpO_2$ sensor, or a combination thereof.

12. The wearable device of claim 9 further comprising:
    a voltage regulator connected to the one or more batteries for providing a stable voltage to the microcontroller;
    a Bluetooth module for allowing the microcontroller to send the collected data to a user interface; and
    a flexible printed circuit board, on which the microcontroller, the voltage regulator, the Bluetooth module are mounted.

13. The wearable device of claim 12, wherein the one or more batteries are configured to provide a voltage of 2.5V to 5.2V; and the voltage regulator is configured to provide the stable voltage with 3.3V.

14. The wearable device of claim 12, wherein the one or more batteries include four batteries.

15. The wearable device of claim 12 further comprising:
    a first flexible layer arranged to cover a skin of the user; and
    a second flexible layer, the flexible printed circuit board being located between the first flexible layer and the second flexible layer.

16. The wearable device of claim 15, wherein the first flexible layer comprises a hole accommodating the one or more sensors.

17. The wearable device of claim 12 further comprising:
    two conductive wires for connecting the one or more batteries to the flexible printed circuit board; and
    a flexible substrate comprising one or more holes accommodating the one or more batteries.

18. The wearable device of claim 12, wherein the user interface is a smartphone application contained in a smartphone.

* * * * *